(12) United States Patent
Winqvist

(10) Patent No.: US 7,658,731 B2
(45) Date of Patent: Feb. 9, 2010

(54) DISPOSAL MEANS ON AN ABSORBENT DIAPER

(75) Inventor: Pontus Winqvist, Stora Höga (SE)

(73) Assignee: SCA Hygiene Products AB, Gothenburg (SE)

( * ) Notice: Subject to any disclaimer, the term of this patent is extended or adjusted under 35 U.S.C. 154(b) by 451 days.

(21) Appl. No.: 10/972,655

(22) Filed: Oct. 26, 2004

(65) Prior Publication Data

US 2005/0090793 A1    Apr. 28, 2005

Related U.S. Application Data

(60) Provisional application No. 60/514,478, filed on Oct. 27, 2003.

(51) Int. Cl.
*A61F 13/15* (2006.01)
(52) U.S. Cl. .............................. 604/385.13; 604/385.03
(58) Field of Classification Search ............ 604/385.13, 604/385.03, 385.02, 385.201
See application file for complete search history.

(56) References Cited

U.S. PATENT DOCUMENTS

| 3,559,648 | A | * | 2/1971 | Mason, Jr. .................. 604/375 |
| 3,848,594 | A | * | 11/1974 | Buell .......................... 604/390 |
| 3,920,019 | A | * | 11/1975 | Schaar .................. 604/385.13 |
| 4,681,581 | A | * | 7/1987 | Coates ........................ 604/391 |
| 4,963,140 | A | * | 10/1990 | Robertson et al. ............ 604/389 |
| 6,063,067 | A | * | 5/2000 | Takizawa et al. ............ 604/386 |
| 6,743,213 | B1 | * | 6/2004 | Minato ........................ 604/390 |

FOREIGN PATENT DOCUMENTS

| EP | 0 529 681 A1 | 3/1993 |
| EP | 0 732 094 B1 | 9/1996 |
| JP | 2000 014698 A | 1/2000 |
| JP | 2002 238950 A | 8/2002 |

OTHER PUBLICATIONS

International Preliminary Examination Report issued in a corresponding application, May 11, 2006.

* cited by examiner

*Primary Examiner*—Tatyana Zalukaeva
*Assistant Examiner*—Lynne Anderson
(74) *Attorney, Agent, or Firm*—Buchanan Ingersoll & Rooney PC

(57) ABSTRACT

An absorbent diaper (1) has a topsheet (5) and a backsheet (6) and an absorbent core (7). The diaper also has a rear waist portion (4), and a front waist portion (2), each having an upper edge respectively (8,9). The diaper further has a disposal tape (14) which is attached to both the topsheet (5) and the backsheet (6) across and around an upper edge (8, 9). One of the attachments (17) is releasable. The disposal tape (14) may be used for maintaining the diaper in a rolled or folded configuration for disposal, while before being used for disposal it covers an upper edge (8, 9) of the diaper, providing a comfortable upper edge for the wearer.

24 Claims, 6 Drawing Sheets

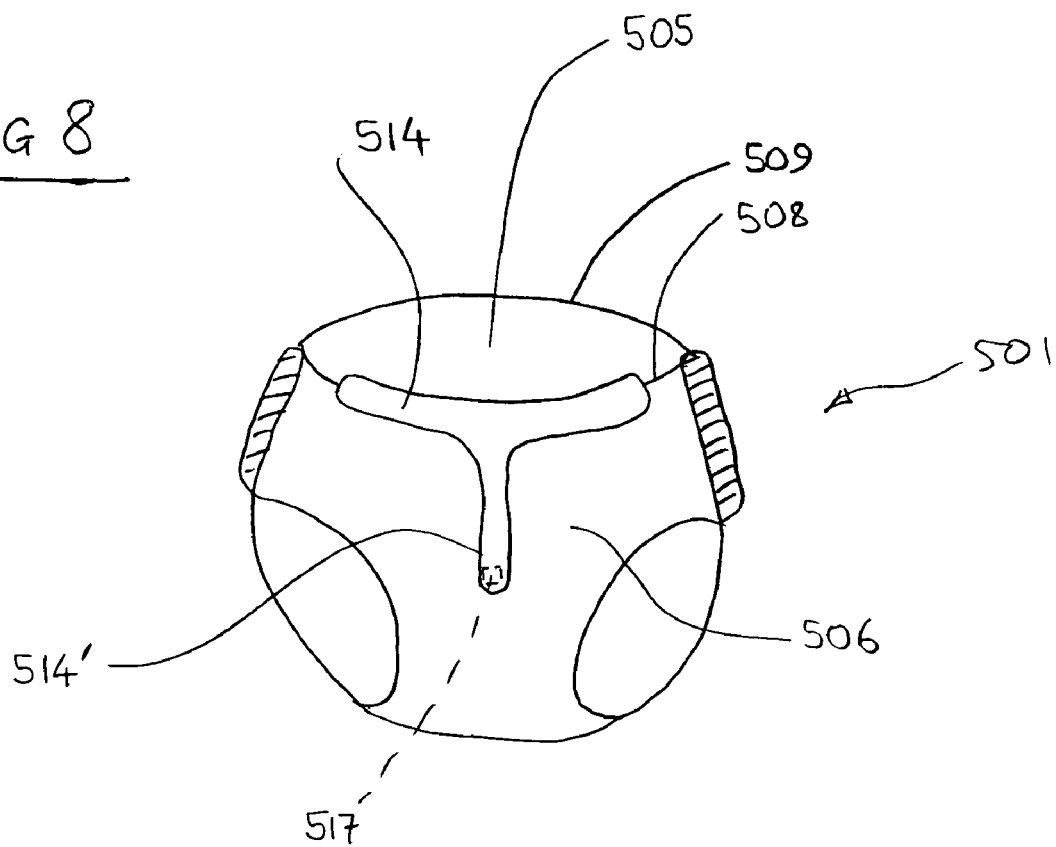
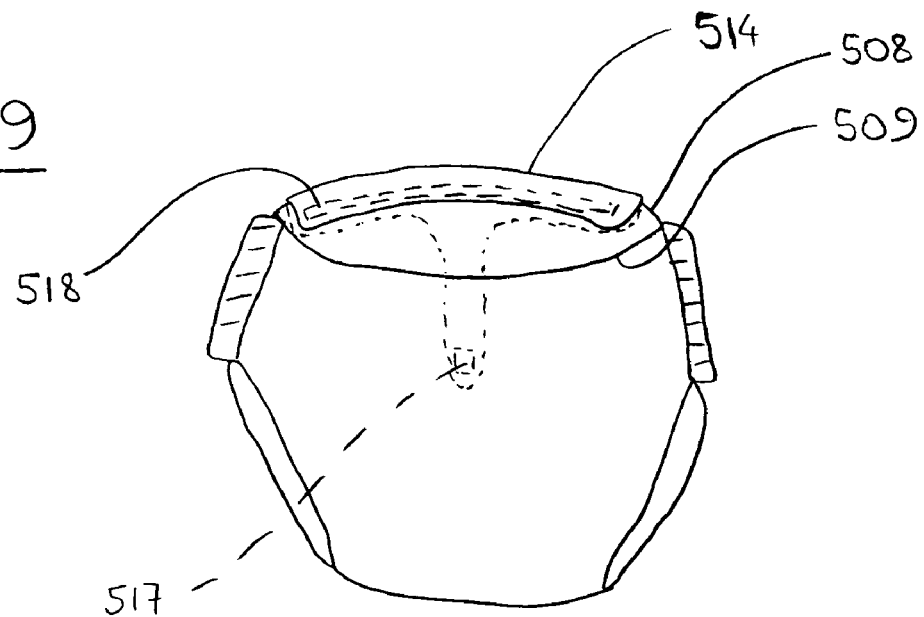

DISPOSAL MEANS ON AN ABSORBENT DIAPER

CROSS-REFERENCE TO RELATED APPLICATIONS

The present application claims the benefit of U.S. Provisional Application No. 60/514,478, filed in the United States on Oct. 27, 2003, the entire contents of which are hereby incorporated herein by reference.

FIELD OF THE INVENTION

The present invention relates to an absorbent diaper having a disposal means. In particular, the invention relates to a disposable absorbent diaper of the type having a closure means for fastening front and rear waist portions of the diaper together provided with such a disposal means in the form of a disposal tape, or to a disposable absorbent pants-type diaper provided with a disposal tape.

BACKGROUND OF THE INVENTION

Absorbent diapers having closure means for fastening front and rear portions together and of the pants type are known for example from EP-A-0 732 094. Also known in the art are pants-type diapers with reclosable sides, whereby additional side fastening means are provided which, after tearing open one or both of the sides, allow for reclosure of the open sides.

Once a diaper has been used, normally after having first been soiled, it is removed from the user and folded or rolled up to maintain the exudate contents within the diaper. In order to maintain the diaper in a closed state, the side fastening tapes of a side-fastening diaper may each be used to hold the diaper in a closed configuration. This may be done either by, for example, tensioning and joining the side fastening tapes to each other across the outer surface of the closed diaper, or if the backsheet of the diaper is suitable the fastening tapes can each be joined to the back sheet of the closed diaper to keep it closed. In a pants-type diaper, a special disposal means is normally provided since there are typically no side fastening tapes. Such a disposal tape, as shown in the aforementioned EP-A-0 732 094, may then be used. The tape is attached to the backsheet or the topsheet at a laterally middle portion of one of the upper waist edges of the diaper. When the diaper is to be disposed of, the tape is opened and then extended by deforming it, including plastically deforming it, so as to provide a length of tape which can be tied around the closed diaper or adhered with its opposite end to the backsheet of the closed diaper so as to maintain the diaper closed.

Diapers of both the side fastening and pants-type each comprise a front and rear waist portion, which is typically elasticated. The upper edge, in particular of the front waist portion, can be uncomfortable for a wearer when the wearer moves due to the upper edge being relatively narrow, somewhat rigid (especially due to the elastication) and sometimes even relatively sharp. In certain cases, the upper edge of the waist portion may chafe or cut into the wearer's skin. This problem may be particularly accentuated in the laterally central portion of the front waist portion upper edge (i.e. that portion approximately located in line with the wearer's navel when worn).

OBJECTS AND SUMMARY

One of the objects of the present invention is to provide a diaper with an improved upper edge configuration for at least part of an upper waist edge.

A further object of the invention in relation to diapers of the pants-type is to provide said improved upper edge configuration with a minimum of extra material.

The absorbent diaper is defined in terms of a rear waist portion and front waist portion, these terms being used to define the portions of the diaper intended to be positioned against the wearer's back and stomach portions, respectively, during use. A disposal tape used with the diaper of the present invention may however be attached to the rear and/or the front waist portion.

The disposal tape according to one embodiment may be attached at the front waist portion of the diaper. More particularly, the disposal tape may be positioned at the laterally central portion of the front and/or rear waist portion(s) of the diaper, so as to give a wider and preferably softer upper edge at the central portion(s). In this regard, the lateral direction is the direction running from one waist portion side edge (located above the hip) to the other side edge, and the central portion defines a portion of the diaper located generally centrally between the side edges. In most cases, the disposal tape will be located along, or close to, the longitudinal axis of the diaper which runs centrally between the front and rear waist portions.

The disposal tape is preferably attached fixedly, generally at one end portion thereof, and releasably attached generally at the other end portion thereof, to respective portions of the diaper. In this regard, the term fixedly attached is intended to mean an attachment which is not intended to be pulled apart during normal use and which, if pulled apart, generally results in destruction of one of the layers to which it is attached and is not intended to be re-attached. Such attachments may be formed e.g. by welding. A releasable attachment is an attachment which is intended to be not only attached but also removed (i.e., detached) and re-attached. Such releasable fastenings are well known per se in the art and are preferably in the form of a releasable mechanical fastener. Such releasable mechanical fasteners are most commonly of the hook and loop type (an example of which is Velcro®). Such hook and loop fasteners include the type where the elements are not strictly in the form of hooks or loops, e.g. mushroom shaped heads for instance. Many variations of such releasable mechanical fasteners exist which are suitable for use with the diaper of the invention which will be apparent to a skilled person. Mechanical engagement fasteners of the type which include rigid elements such as a button/button-hole combination, or press studs or the like, are not intended to be included in the terminology releasable mechanical fasteners.

The front and/or rear waist portion of the diaper may be provided with waist elastic to provide additional comfort.

The disposal tape of the inventive diaper may be elastic. The disposal tape is considered to be elastic if it can be elastically extended by more than 50% without substantial permanent strain, whereby substantial permanent strain is understood as being of the order of more than about 10% of the initial length at the first stretching, when held stretched for a period of time less than 5 minutes.

BRIEF DESCRIPTION OF THE DRAWINGS

The invention will now be explained in more detail with reference to certain non-limiting embodiments thereof and with the aid of the accompanying drawings, in which:

FIG. 8 shows a further embodiment of a view similar to FIG. 3 with an alternative form of disposal tape.

FIG. 9 shows a view of the rear waist portion of the diaper of FIG. 8.

DETAILED DESCRIPTION OF THE PREFERRED EMBODIMENTS

Figure 1:
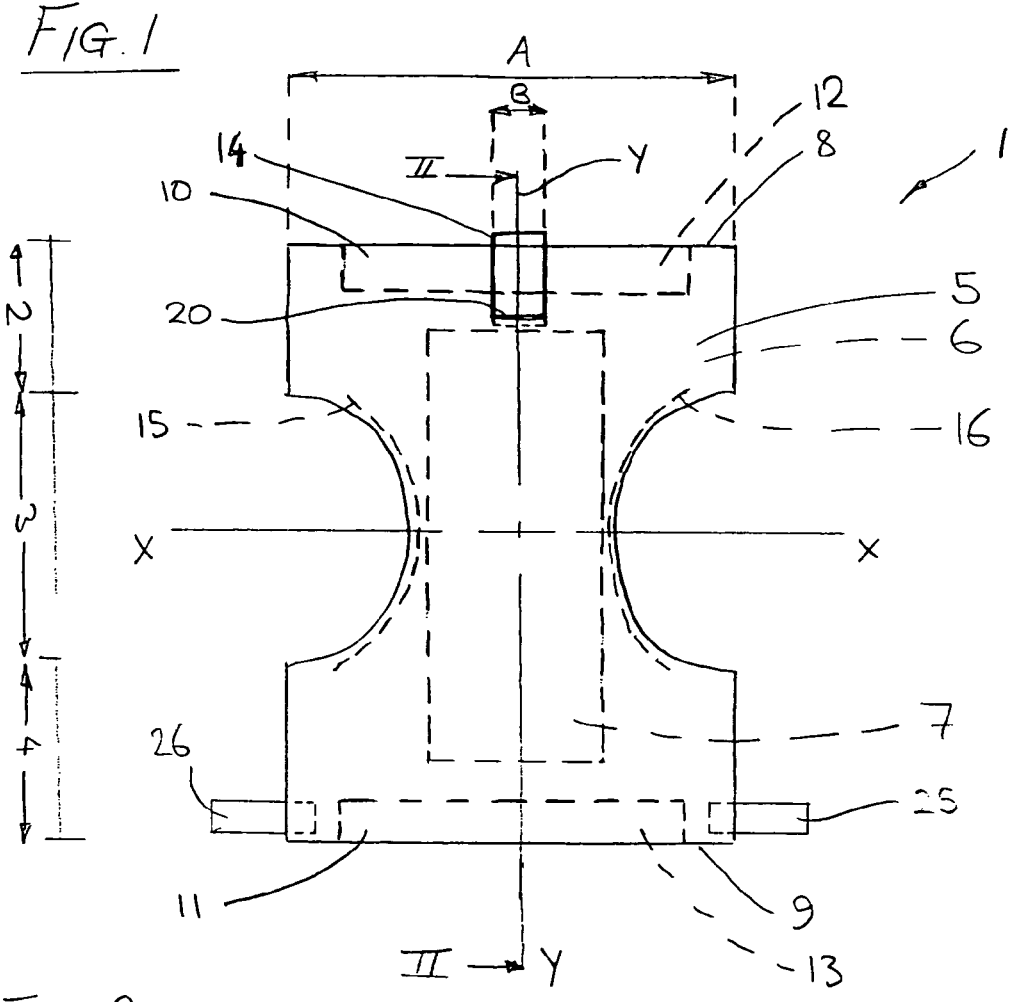
FIG. 1 shows a reclosable diaper in accordance with an embodiment of the invention, in a laid-flat condition.

FIG. 1 shows a view of one embodiment of a laid-flat diaper according to the invention looking onto the body-facing surface of the diaper. The diaper 1 comprises a longitudinal axis Y-Y and a lateral axis X-X extending generally perpendicular thereto. In the longitudinal direction, the absorbent product 1 is divided into three portions, a front waist portion 2, a middle or crotch portion 3 and a rear waist portion 4. The diaper front waist portion 2 is intended to be placed against the user's front waist during use. With the front and rear waist portions 2, 4 located on the user, the fastening tapes 25, 26 fixedly located on the back sheet 6, and containing preferably releasable attachment (not shown) at their free ends, are then fastened to the backsheet of the front waist portion in a conventional and well-known manner so as to close the sides of the diaper on the wearer.

The longitudinal axis Y-Y passes generally through the mid points of each of these three portions 2, 3, 4.

The upper or body-facing surface is constituted by a liquid-permeable top sheet 5. The opposite surface, an undergarment-facing surface, is constituted by a liquid impermeable back sheet 6 which is preferably co-extensive with the top sheet 5 and sealed to the top sheet 5 at the peripheries of both of said sheets, e.g., by welding or adhesive or other fixed attachment. In between the back sheet 6 and the top sheet 5 there is an absorbent core 7. The possible structures, materials and shapes of the top sheet 5, back sheet 6 and absorbent core 7 can be widely varied by a skilled person, and many possibilities are already known in the art.

The front waist portion 2 of the diaper comprises an upper edge 8 which extends laterally by a distance A as shown in the Figure, namely from one waist side edge to the other waist side edge. The rear waist portion 4 also comprises two side edges and a lateral edge, said lateral edge referred to herein as upper edge 9 (due to its ultimate position, during use, at the upper edge of the wearer's waist) and which typically will extend equidistantly to upper edge 8.

In the front waist portion 2 and/or the rear waist portion 4, there is preferably a first elasticated waist section 10 and a second elasticated waist section 11 respectively. The waist elastic 12, 13 respectively, where present, preferably allows an extension of up to 50% or more to allow the user's movements, when standing and sitting for example, to be taken into account while still providing a comfortable and well-fitting waist portion. The waist elastic, when present, is preferably located outside the longitudinal limits of the absorbent core 7 so that any bunching together of the absorbent core 7 by the elastic forces in the waist elastic is minimized. The waist elastic may, if desired, be partially or entirely located in an area of the waist portion which lies outside the boundaries of the disposal tape 14, in order to avoid any bunching of the disposal tape 14 where the disposal tape 14 is attached in the diaper 1.

Leg elastics 15 and 16, and other elastics such as elasticated ears (not shown) may also be included. Furthermore other diaper features may also be included such as standing gathers, faecal pockets, and other gusset formations for example, although these are not shown or described in further detail herein as they are well known to a skilled person and are not directly related to the inventive product.

At least one disposal tape 14 is positioned generally centrally in a lateral direction (X-X) at the front waist portion 2 or at the rear waist portion 4. At least one disposal tape 14 may also be positioned at both the front and rear waist portions 2, 4. Generally however, only one disposal tape 14 is required, positioned for example at the front waist portion 2.

The disposal tape 14 has a lateral width B (see FIG. 1) at the location where it passes across and around the upper edge 8, where B≦A. In its simplest form, the disposal tape 14 is a generally rectangular strip of constant dimension B along its entire length (Y-Y direction), although this is not a requirement. The tape may also be oval (not shown) or another shape such as hourglass shape, or any other desirable shape from a functional or aesthetic point of view.

The dimension B may be as small as 2 cm in the portion where it passes across and around the waist upper edge 8, although it is preferably greater than 2 cm, more preferably greater than 5 cm and may be up to 15 cm, or even more. Dimension B may advantageously be chosen to extend by 50% or more of dimension A so as to cover a major portion of upper edge 8.

Figure 2:
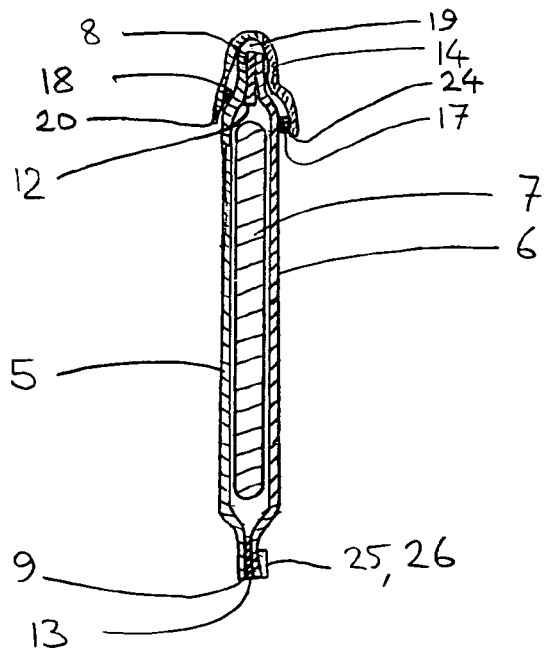
FIG. 2 shows a cross-sectional view along line II-II in FIG. 1.

As shown clearly in FIG. 2, the disposal tape 14 is attached to the backsheet 6 by attachment 17 and to the topsheet 5 by means of the attachment 18. Each of the attachments 17, 18 may be constituted by single areas of attachment or multiple areas of attachment (e.g., at spaced locations). The attachment means 17 and 18 may each be a releasable attachment, although it is preferred that one of the attachments is a fixed attachment. Preferably, the attachment 18 should be a fixed attachment between the strip 14 and the topsheet 5, since this portion of the disposal tape 14 is closest to the wearer's skin. It is thus possible that exudate will be on the tape 14 at that particular location when using the disposal tape 14 to dispose of the diaper 1. Thus, to avoid handling the end portion of the disposal tape closest to the wearer when using the disposal tape 14, it is preferred that this end portion is fixed and that the opposite end portion attachment 17 is releasable. The manner of using the disposal tape will be explained below.

The disposal tape, in its position before the diaper is worn, is attached to the body-facing surface and the undergarment-facing surface while it is positioned across and around the upper edge 8.

The location of the fixed attachment 18 on the tape end portion is not critical, although this is preferably located close to the longitudinal end 20 of the disposal tape. If required, for reasons of strength, the attachment 18 may extend over a major part of the end portion of the tape 14, even up to the upper edge 8, although it is preferred that a small margin of non-attachment be left below the upper edge 8 to avoid any hard edge effect being created.

The releasable attachment 17 may be a pressure sensitive adhesive or a releasable mechanical fastening for example. Whatever is chosen, the releasable attachment 17 should be capable of attaching to either the outer surface of the disposal tape 14 (e.g. after having been passed around the rolled or folded-up diaper) and/or to the backsheet of the diaper. Where the releasable attachment 17 is a pressure sensitive adhesive, the backsheet 6 and/or tape 14 may be of polyethylene or other polymeric film material or any other material to which the pressure sensitive adhesive will attach. If the releasable attachment is a hook portion of a hook and loop type attachment, then the backsheet 6 and/or the disposal tape 14 outer surface should be made of a suitable receiving material, such as nonwoven fabric, to which the hook portion will readily attach with only light pressure.

The material of the disposal tape 14 should preferably be such that a soft outwardly-facing surface is provided for contact with the wearer. Thus, although ordinary adhesive tape films could be used (e.g., an extruded polyethylene or polypropylene film) as the disposal tape, such tape material is less preferred for the diaper of the invention since it is not particularly soft.

Preferred materials for the disposal tape are nonwoven materials or foam materials. Single layer nonwoven materials may be used for example, such as spunbond, meltblown or carded nonwoven.

In some embodiments, nonwoven laminates may be used. One example particularly suitable for the invention is a spunbonded/carded nonwoven where the carded layer of the laminate should be the layer of the laminate which contacts the skin during use. For this laminate, the following layers may be used, namely a spunbonded, 100% polypropylene, white, 30 gm$^{-2}$ surface weight layer, 2.2 to 2.5 dtex, while the carded layer may by a white, 100% polypropylene, 2.2. dtex, layer of 30 gm$^2$ surface weight.

However, a surface weight of less than 30 gm$^2$ may be used since the tension on a disposal tape is not normally very high. Thus a lower surface weight of e.g. 18 gm$^2$ is normally acceptable. Surface weight in the range of between 15 gm$^2$ and 80 gm$^2$ is thus preferred for the whole tape, and more preferably between 20 and 65 gm$^2$, so as to meet the requirements of both strength and softness. Surface weight measurements should be made using dry materials at a temperature of 21° C. and humidity conditions of 55%.

The carded layer mentioned above (white, 100% polypropylene, 2.2. dtex between 18 and 30 gm$^{-2}$) may also be used as the garment-facing surface layer, to which a hook like material section (of a hook and loop type attachment) of the disposal tape may releasably attach.

Where foam materials are used for the disposal tape, suitable materials may be polyurethane (PU) or polyethylene (PE) foams for example. However, the type of foam should be chosen preferably to be soft, at least in the portion which is intended to contact the wearer's skin. A suitable foam thickness for PU or PE foams typically lies between 0.5 mm and 8.0 mm (as measured by an optical calliper without compression). Thick foam material (e.g. up to 8 mm or even more) can be preferred as this is generally softer than thin foam materials, since larger pores (cells) may be present. Open celled foam or closed celled foam can be used.

Since the disposal tape 14 extends along the body-facing surface at the waistband (front waist portion and/or rear waist portion), at least this part of the disposal tape may be constructed to be an absorbent member. In such a case, open celled foam is preferred due to its absorbent properties. The portion of the disposal tape at least at the body-facing surface of the diaper may thus function to prevent escape of body exudates by temporarily holding and absorbing same at the waist region. Since the risk of leakage of exudate is often greater at the rear waist portion, the use of an absorbent disposal tape at least at the rear waist portion of the diaper may be particularly advantageous. A further advantage is provided when having the disposal tape at the rear waist portion of the diaper, namely since it is more difficult for the wearer to release the disposal tape. In the case of small children for example, providing a disposal tape at the rear (which is thereby more difficult to detach) can provide advantages in that the child cannot easily intentionally release the disposal tape.

As shown in FIG. 2 for example, a distance may be left between the lowermost edge 20 of the disposal tape 14 and the attachment 18 which may thereby be arranged to form a pocket for receiving exudate. Such a pocket also allows more time for the foam material to absorb any exudate present in that region of the diaper.

In this regard it is noted that dimension B of the tape 14 depicted in FIG. 1 extends only a small extent of the length of upper edge A, and that where the disposal tape 14 is intended to serve as a pocket and/or as an absorption member, the dimension B should be made longer, preferably at least 50% of dimension A and more preferably at least 75% of dimension A. In certain diapers, for heavy incontinence for example it may be desirable to provide dimension B to be the same as dimension A.

It is highly desirable that the foam material is one chosen to be flexible in its dry condition. PU and PE foams which are flexible are well known in the art. In cases where the foam is less flexible, sufficient flexibility can normally be achieved by making the foam thinner.

Although the Figures show that the portion of the disposal tape 14 overlying the garment-facing surface and that overlying the body-facing surface are approximately equal, it may be preferable if the length of the disposal tape 14 in the Y-Y direction on the garment-facing surface is greater than that on the body-facing surface. In this way, more tape length is available for reattachment of the attachment means 17 of the disposal tape 14 to the backsheet 6 after rolling up the diaper.

Although not a requirement, where the disposal tape 14 passes across and around the upper edge 8, an excess of material may be provided such that a small air pocket is created. This may have the advantage of increasing the softness and feel of the tape at the upper edge 8 when in contact with the wearer's skin.

The length of the tape (i.e. the dimension in the Y-Y direction) may be as short as 2 cm, although the length is preferably greater than 5 cm. Longer tapes may also be used, e.g. 10 to 20 cm if it is desired for example to pass the tape around the whole circumference of a rolled up diaper to be disposed. The material of the tape may also be chosen to be elastically extensible, at least along one or more portions thereof, or along the whole length thereof, such that a shorter disposal tape 14 can be used.

In some cases (see e.g. FIGS. 8 and 9, to be explained in more detail below) the length of the wide portion of the disposal tape 14 which passes across and around the front waist portion upper edge 8 may cover a major portion of the upper waist edge with an overlap on either side of the edge by only a small amount (e.g. 0.5 cm to 2 cm) while a further portion of the disposal tape (e.g. in the laterally central section as shown in FIGS. 8 and 9) may be longer.

Figure 3:
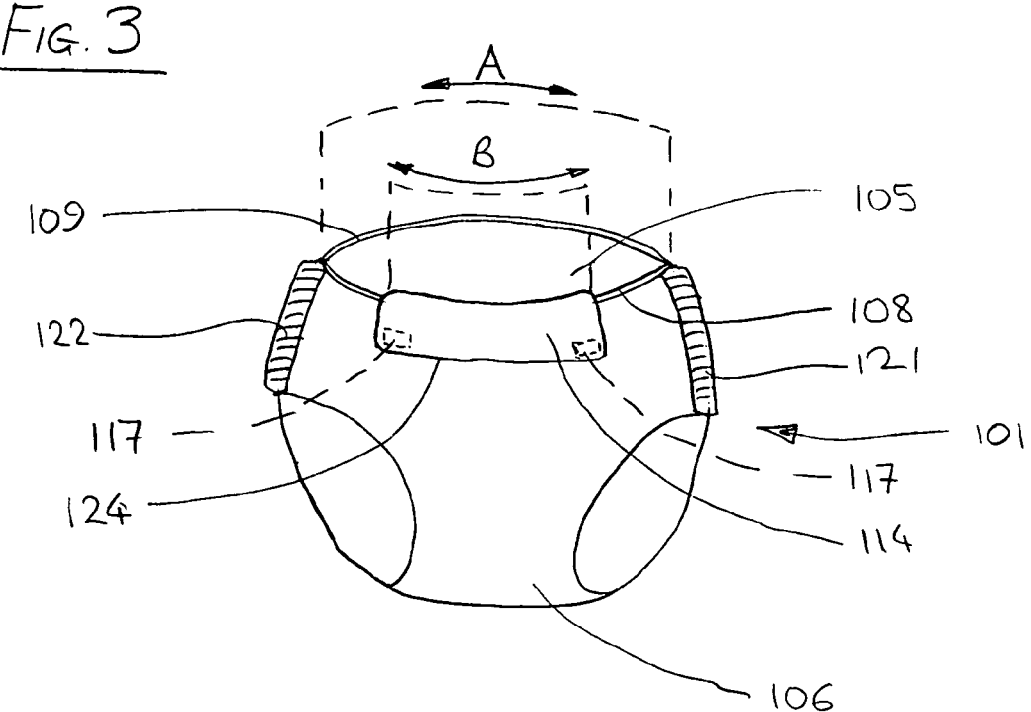
FIG. 3 shows a view of the front waist portion of a pants-type diaper depicting a disposal tape in the laterally central portion.
Figure 4:
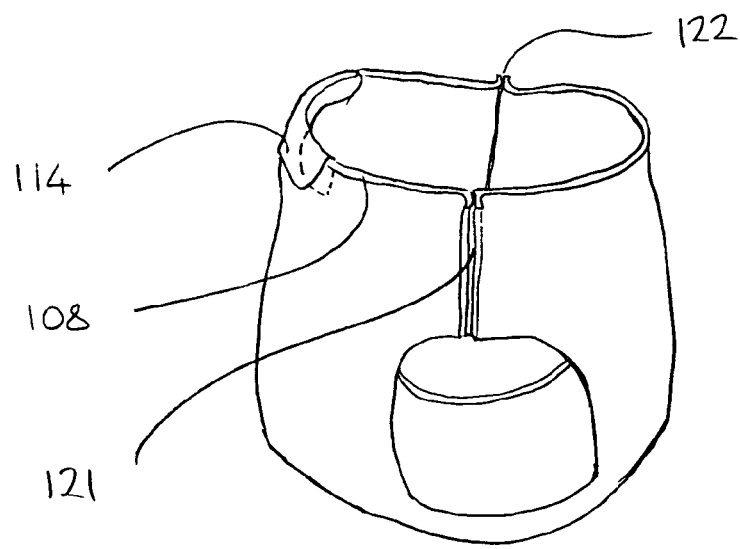
FIG. 4 shows a side perspective view of the diaper in FIG. 3.

A further embodiment of the diaper according to the invention in the form of a pants-type diaper 101 is shown in FIGS. 3 and 4 in a perspective front view and side view respectively. The reference numerals in FIGS. 3 and 4 correspond to those used in FIGS. 1 and 2 but are raised by 100.

The pants-type diaper 101 has the side edges of the rear waist portion and the front waist portion joined together at seams 121, 122. Typically these seams are welded seams or seams formed by adhesive between the side edges. The seams, in some embodiments, may be made such that they can be peeled or torn open and side reclosure means (not shown) may additionally be provided to allow reclosure after opening the sides.

The lateral dimension B of the disposal tape 114 is, in this embodiment, shown to extend approximately 50% of the length of the upper edge (dimension A). However a smaller or larger dimension B relative to dimension A may be chosen. By choosing a larger dimension B, the upper edge 108 is obviously covered to a larger degree, thus allowing the material of the disposal tape to form a soft and comfortable upper edge in contact with the wearer's body in the major area of contact with wearer and the area which is perhaps most susceptible to higher pressure from the wearer.

In this embodiment, due to the width B (in the X-X direction) of the disposal tape, two attachments 117, preferably releasable attachments, are provided at the end portion of the tape 114 close to the outer lower edge 124 at spaced locations therealong. However it will be apparent that a single attachment 117, or more than two attachment means 117, could be provided if desired.

If the attachment 117 is instead a fixed attachment means between the disposal tape 114 and the back sheet 106, a releasable attachment (not shown) must be provided to connect the disposal tape 114 to the body-facing surface 105 of the diaper (at a location thereon which may for example be at the corresponding location shown in the first embodiment of FIGS. 1 and 2 by attachment 18).

The rear waist portion upper edge 109, as in the first embodiment, has no disposal tape member thereon. A disposal tape of either the same dimensions or differing dimensions to disposal tape 114 may also/alternatively be provided at the rear waist portion. In this way, the rear waist upper edge 109 can be made more comfortable for the wearer.

Figure 5:
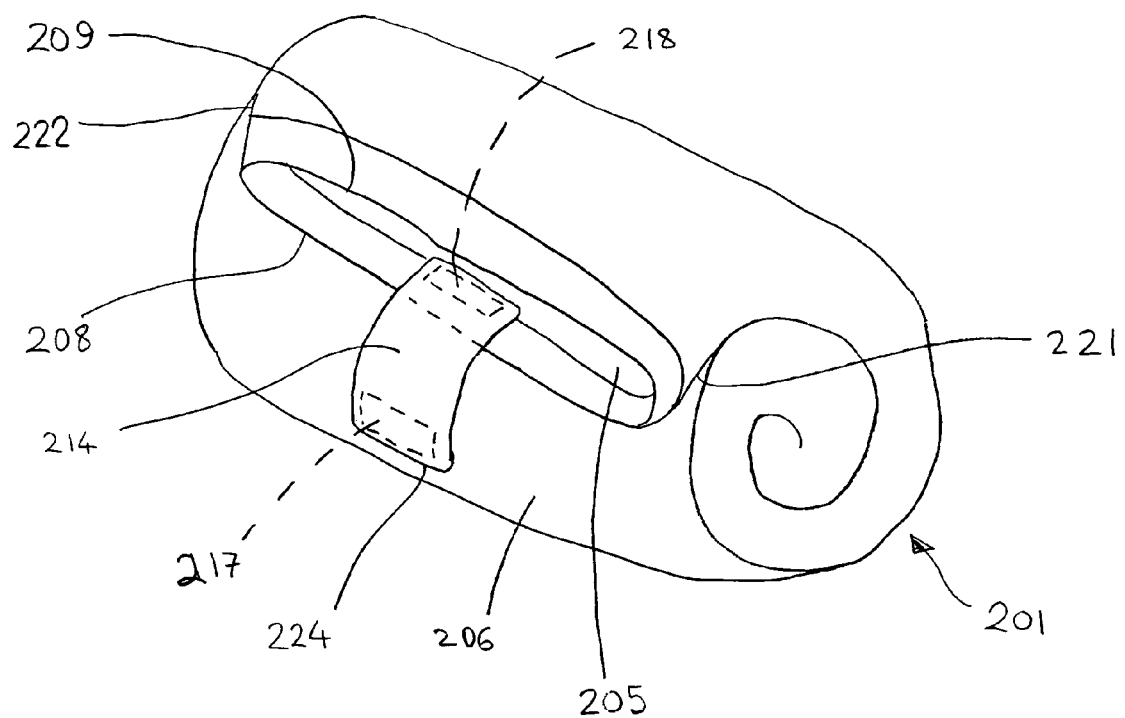
FIG. 5 shows an example of a pants-type diaper rolled up for disposal and with the disposal tape fixedly attached to the body facing surface and attached to the backsheet.

When the disposal tape is used for holding the diaper in a certain condition for disposal, the diaper may be in a configuration with the waist side edges open or closed. The disposal of a diaper and use of the disposal tape will now be described in relation to a diaper as shown in FIG. 5. FIG. 5 uses corresponding reference numerals as in previous embodiments starting however with numeral 201. In FIG. 5, the waist portion side edges are attached at joint areas 221, 222 as they are in the embodiment in FIGS. 3 and 4. However it will be understood that the waist portion side edges may be either attached (pants-type) or separated (closable/reclosable types), so that the rolled up configuration shown in FIG. 5 applies to diapers with either open or closed waist side edges.

With the diaper in a configuration where the front and rear waist portions are placed against each other, whereby the topsheet areas at each of these portions contact one another, exudate is generally contained within the diaper on the body-facing surface and thus not exposed externally. The product 201 can then be folded one or more times, and/or rolled up as shown for example in FIG. 5. The releasable attachment 217 is released (either before or after folding/rolling up) so that the end of the disposal tape 214 with the releasable attachment 217 thereon (i.e., the end portion including lower edge 224) can be releasably attached to the backsheet 206 to maintain the diaper in its configuration for being disposed. The diaper product is thus ready for disposal in the configuration shown in FIG. 5.

Figure 7:
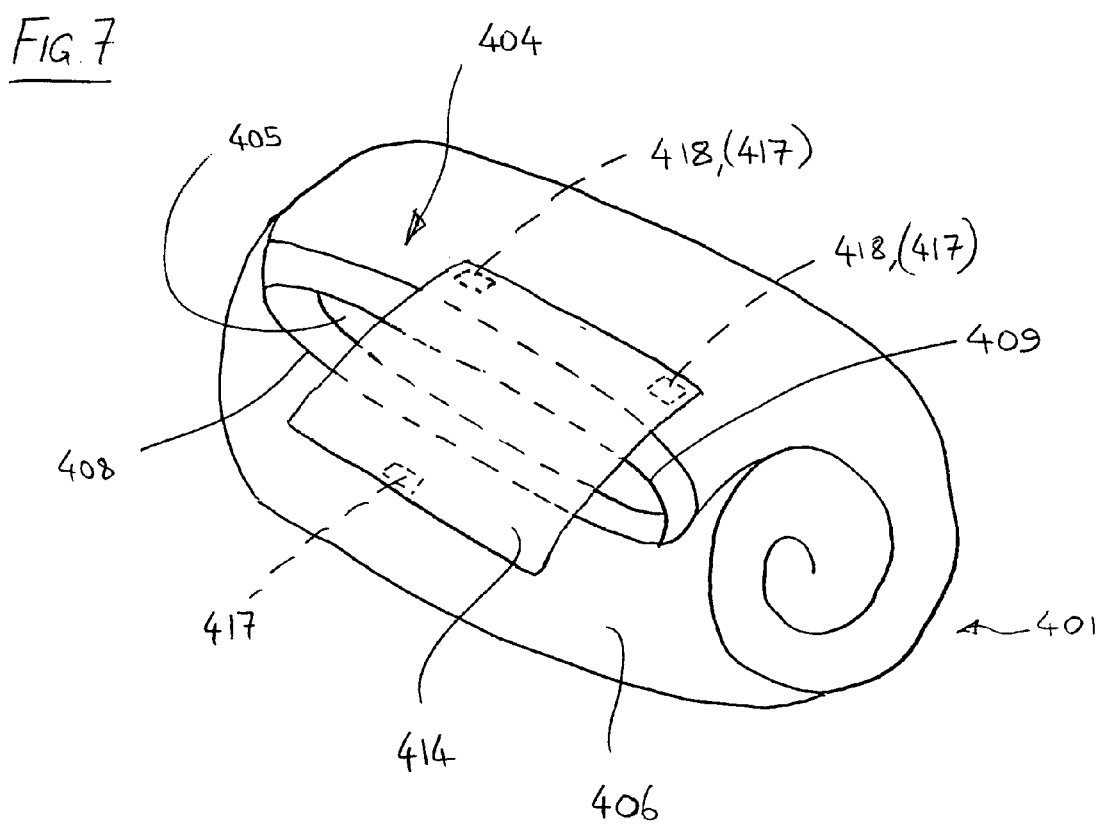

As will be apparent from FIG. 5, if the attachment means 218 is made as a releasable attachment, the disposal tape can be removed from the body-facing surface (topsheet 205) and then the attachment means 218 can be attached to another portion of the backsheet (e.g., across both waist portion upper edges 208, 209), for example so as to close the waist opening as well. Such an embodiment is shown in FIG. 7 (using a somewhat wider disposal tape 414 than that in FIG. 5), whereby a single releasable attachment 417 is located on one part of the backsheet 406 and two releasable 417 (indicated in parentheses in the Figure) are provided at the other end of the disposal tape 414 attached to the backsheet 406 on the other side of the waist opening. In the embodiment of FIG. 7, the two reference numerals 418 indicate a further alternative configuration in which the attachment 418 is a fixed attachment, whereby only the attachment 417 need be released from its originally attached orientation (not shown) where it was releasably attached to the body-facing surface (topsheet 405) of the rear waist portion 404.

Figure 6:
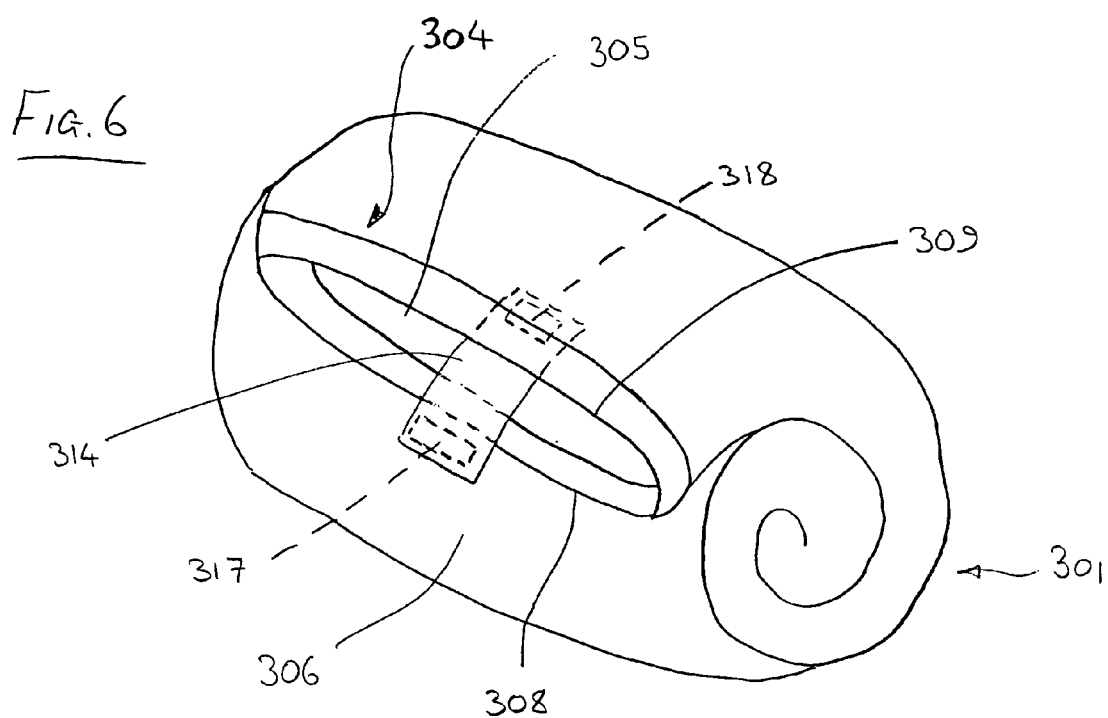
FIG. 6 and FIG. 7 each show a pants-type diaper similar to that in FIG. 5, with alternative disposal tape attachment locations for diaper disposal.

As mentioned above, the disposal tape 214 can be attached (in its condition before disposal) either releasably or fixedly to either the garment-facing surface or the body-facing surface of the diaper at the rear waist portion and/or the front waist portion, as long as at least one of the attachments is releasable and the disposal tape (or each disposal tape, if more than one is provided) extends across and around a single upper edge of the diaper. Thus a plurality of ways of arranging the disposal tape configuration is available. One such configuration is shown in FIG. 6 showing the diaper held together with the disposal tape 314 in a condition for disposal, whereby the disposal tape 314 is fixedly attached to the backsheet 305 on the rear waist portion 304 with a fixed attachment means 318, and a releasable attachment 317 on the tape 314 has been releasably attached to the backsheet 306 thereby passing between upper edges 308, 309. In such a configuration, the releasable attachment 317 is shown in hidden detail which means that, in its initial position on the diaper where it is attached across and around the upper edge 309, a means for releasably fixing the tape 314 to the backsheet across and around that edge 309 is required. This may be in the form of a further releasable attachment (not shown) provided on the tape and/or on the backsheet at that initial location of attachment.

A further alternative (not shown) is that the tape could be provided with only one releasable member 317 (as already shown on the tape in FIG. 6), but that the tape (after release from its initial releasable position on the backsheet 306 at the rear waist portion 302) is twisted through 180° around its longitudinal axis before being placed on the topsheet at the location shown in FIG. 6.

In the embodiment shown in FIGS. 8 and 9, the disposal tape 514, 514' has been given a form which allows improved comfort as regard the upper edge 508 as well as a saving in material, whereby the front waist portion upper edge 508 has sufficient material to cover it over a portion of its length (e.g. more than 25% of its length, preferably more than 50% and more preferably more than 75% of its length) with a small overlap across and around the upper edge while at the same time a longitudinally extending portion 514' of reduced width in the lateral direction (X-X) is used to provide the length of material desired for easy fastening the diaper together. FIG. 9 shows the same embodiment as FIG. 8 from the rear of the diaper and more clearly shows the disposal tape 514 passed around and across the upper edge 508. The attachment means 518 fixedly attaching the disposal tape 514 to the body-facing surface (topsheet 505) around the edge 508 is shown in FIG. 9 as an elongated area, which may extend substantially the entire width of the disposal tape 514, while a releasable attachment to the garment-facing surface (backsheet 506) is shown as a single attachment means 517 on the end portion of longitudinal extension 514'.

Figure 10:
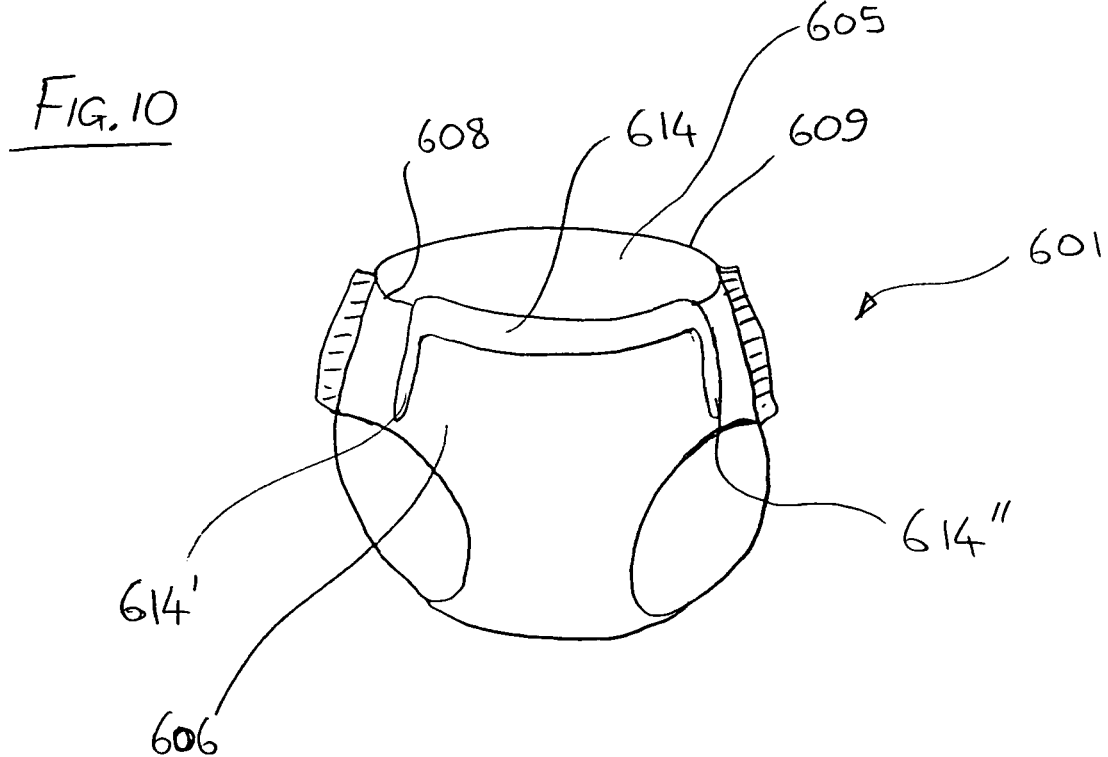
FIG. 10 shows a view similar to that in FIG. 6 but with an alternative form of the disposal tape.

FIG. 10 shows an embodiment similar to that in FIGS. 8 and 9. However, the single longitudinal extension 514' is replaced in FIG. 10 with two longitudinal extensions 614' and 614" spaced apart and located at opposite end of the disposal tape 614. For reasons of clarity, the attachment means on the top sheet 605 and back sheet 606 are now shown but may generally have the same locations as shown in FIG. 9. Alternative locations, shapes, types and sizes of the attachment means are of course possible.

It should also be understood that embodiments showing a location of the disposal tape at the front waist portion may equally include an additional disposal tape at the rear waist portion, which additional disposal tape may be of the same or different shape. It is also possible that the tape shown on the front waist portion may be alternatively placed on the rear waist portion. Likewise embodiments showing a location of the disposal tape at the rear waist portion may equally include an additional disposal tape at the front waist portion, which additional disposal tape may be of the same or different shape. It is also encompassed within the invention that the tape shown in the embodiments on the front or rear waist portion respectively may alternatively be placed on the other of the waist portions only.

Further orientation, shapes and attachment of the tape are possible within the scope of the invention. For example, while the tape has been shown as comprising a single tape material, possibly as a laminated structure, the disposal tape of any of the embodiments may comprise two or more sections in the longitudinal direction which sections differ from one another. For example, the disposal tape may comprise three sections (not shown) in the longitudinal direction, where the middle section is that section which passes across and around the upper edge of the waist portion which can be made particularly soft possibly by using thicker material (e.g. foam material), and where the two outer sections are made of a material which is possibly less soft and cheaper (e.g. polyethylene tape), each of said outer sections being fixedly attached to a respective end of the middle section. Many other material layer/section combinations are also possible.

As will be apparent from the aforegoing, the disposal tape applied in at least certain embodiments of the diaper of this invention has the particular advantage in that it provides a dual function of being a disposal means as well as a means for providing a comfortable edge configuration to the upper waist edge(s).

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. An absorbent diaper comprising a top sheet with a body-facing surface, a back sheet with an undergarment-facing surface and an absorbent core therebetween, said diaper further comprising a rear waist portion, and a front waist portion, each of said waist portions comprising an upper edge wherein said diaper further comprises a disposal tape attached to at least one of said waist portions, said disposal tape is a single, unitary piece of material with fastenings including a single diaper-facing surface, wherein said disposal tape diaper-facing surface is directly attached to both said body-facing surface and said undergarment-facing surface across and around one of said upper edges, said disposal tape extends across the upper edge of at least one of said waist portions along at least 50% of said upper edge, and a gap is provided between a lowermost edge of the disposable tape and one of the fastenings to the body-facing surface to form a pocket configured to receive exudate.

2. The absorbent diaper according to claim 1, wherein said body-facing surface comprises a liquid-permeable layer and said undergarment-facing surface comprises a liquid-impermeable layer.

3. The absorbent diaper according to claim 1, wherein said disposal tape is attached to said body-facing surface and said undergarment-facing surface such that said disposal tape at least covers a laterally central portion of one of said upper edges.

4. The absorbent diaper according to claim 1, wherein said disposal tape is attached to said body-facing surface or said undergarment-facing surface such that said disposal tape at least covers a laterally central portion of one of said upper edges.

5. The absorbent diaper according to claim 1, wherein a first portion of said disposal tape is fixedly attached to one of said body-facing surface and said undergarment-facing surface, and a second portion of said disposal tape is releasably attached to the other of said body-facing surface and said undergarment-facing surface.

6. The absorbent diaper according to claim 5, wherein said disposal tape is fixedly attached to said body-facing surface.

7. The absorbent diaper according to claim 5, wherein said second portion of said disposal tape comprises a hook attachment member of a hook-and-loop type releasable attachment.

8. The absorbent diaper according to claim 1, wherein said disposal tape comprises nonwoven material or foam material, at least in a portion of said disposal tape located between the upper edge of the waist portion and a point of attachment of the disposal tape to the body-facing surface.

9. The absorbent diaper according to claim 1, wherein said disposal tape is elastically extensible.

10. The absorbent diaper according to claim 1, wherein said garment-facing surface comprises a backsheet of nonwoven material.

11. The absorbent diaper according to claim 1, wherein said diaper is a pants-type diaper.

12. The absorbent diaper according to claim 1, wherein said diaper is a disposable diaper.

13. The absorbent diaper according to claim 1, wherein said disposal tape extends in a direction along the upper edge of said waist portion between 2 and 15 cm.

14. The absorbent diaper according to claim 1, wherein said disposal tape is adapted to serve as an absorption member.

15. The absorbent diaper according to claim 1, wherein said disposal tape extends across the upper edge of at least one of said waist portions along at least 75% of said upper edge.

16. An absorbent diaper comprising a body-facing surface, an undergarment-facing surface and an absorbent core therebetween, said diaper further comprising a rear waist portion, and a front waist portion, each of said waist portions comprising an upper edge wherein said diaper further comprises a disposal tape fastener system attached to at least one of said waist portions, said disposal tape fastener system consisting of a single, unitary piece of material with fastenings, the piece of material having a single diaper-facing surface, wherein said diaper-facing surface is attached to both said body-facing surface and said undergarment-facing surface across and around one of said upper edges, and said disposal tape fastener system extends across the upper edge of at least one of said waist portions along at least 50% of said upper edge, and a gap is provided between a lowermost edge of the disposable tape fastener system and one of the fastenings to the body-facing surface to form a pocket configured to receive exudate.

17. The absorbent diaper according to claim 16, wherein said disposal tape extends across the upper edge of at least one of said waist portions along at least 75% of said upper edge.

18. The absorbent diaper according to claim 16, wherein said disposal tape is adapted to serve as an absorption member.

19. An absorbent diaper comprising a body-facing surface, an undergarment-facing surface and an absorbent core therebetween, said diaper further comprising a rear waist portion, and a front waist portion, each of said waist portions comprising an upper edge wherein said diaper further comprises a disposal tape attached to at least one of said waist portions, wherein said disposal tape is attached to both said body-facing surface and said undergarment-facing surface across and around one of said upper edges;

wherein said disposal tape comprises nonwoven material and foam material, at least in a portion of said disposal tape located between the upper edge of the waist portion and a point of attachment of the disposal tape to the body-facing surface.

20. The absorbent diaper according to claim 19, wherein said non-woven material extends substantially the entire length of said disposal tape with a surface weight of said nonwoven material lying in the range 10 $g/m^2$ to 80 $g/in^2$.

21. The absorbent diaper according to claim 19, wherein said non-woven material extends substantially the entire length of said disposal tape with a surface weight of said nonwoven material lying in the range 15 $g/m^2$ to 65 $g/m^2$.

22. The absorbent diaper according to claim 20, wherein said nonwoven material of said disposal tape is present in a single nonwoven layer.

23. The absorbent diaper according to claim 19, wherein said foam material is polyurethane foam or polyethylene foam, said foam comprising a thickness 0.5 mm to 8 mm.

24. The absorbent diaper according to claim 23, wherein said foam material is open-celled foam.

* * * * *